(12) United States Patent
    Banerjee

(10) Patent No.: US 10,210,955 B1
(45) Date of Patent: Feb. 19, 2019

(54) METHODS FOR DIAGNOSING ZIKA VIRUS

(71) Applicant: Arsh Banerjee, Bayonne, NJ (US)

(72) Inventor: Arsh Banerjee, Bayonne, NJ (US)

(73) Assignee: ARSH BANERJEE, Bayonne, NJ (US)

( * ) Notice: Subject to any disclaimer, the term of this patent is extended or adjusted under 35 U.S.C. 154(b) by 41 days.

(21) Appl. No.: 15/678,515

(22) Filed: Aug. 16, 2017

(51) Int. Cl.
| | |
|---|---|
| *G16H 40/63* | (2018.01) |
| *C07K 14/18* | (2006.01) |
| *A61B 3/12* | (2006.01) |

(52) U.S. Cl.
    CPC .............. *G16H 40/63* (2018.01); *A61B 3/12* (2013.01); *C07K 14/1816* (2013.01)

(58) Field of Classification Search
    USPC ........................................................ 382/128
    See application file for complete search history.

(56) References Cited

U.S. PATENT DOCUMENTS

| | | | | |
|---|---|---|---|---|
| 6,225,348 | B1* | 5/2001 | Paulsen ................ | A61K 9/0048 |
| | | | | 514/530 |
| 7,510,283 | B2* | 3/2009 | Bille .................... | A61B 3/1015 |
| | | | | 351/211 |
| 2014/0038972 | A1* | 2/2014 | Chang .................. | A61K 31/498 |
| | | | | 514/249 |
| 2017/0159026 | A1* | 6/2017 | Kay .................... | A61K 48/0058 |

* cited by examiner

*Primary Examiner* — Gregory F Cunningham

(57) ABSTRACT

A computer implemented method of diagnosing whether a human subject is infected with Zika virus, includes: determining a correlation between a fundus test image of an eye of the human subject for presence of gross macular pigment mottling with a known set of Zika virus infected fundus images and with a known set of healthy fundus images, wherein a high correlation/low correlation between the fundus test image and the known set of Zika virus infected fundus images indicates that there is a high probability/low probability that the human subject is infected with Zika virus, wherein a high correlation/low correlation between the fundus test image and the known set of healthy fundus images indicates that there is a low probability/high probability that the human subject is infected with Zika virus.

15 Claims, 2 Drawing Sheets

METHODS FOR DIAGNOSING ZIKA VIRUS

TECHNICAL FIELD OF THE INVENTION

The present invention generally relates to Zika virus, and more particularly, to methods for diagnosing Zika virus in a human subject through fundus images.

BACKGROUND OF THE INVENTION

Zika virus is a member of the virus family Flavlviridae. It is spread by daytime-active *Aedes* mosquitoes, such as *A. aegypti* and *A. albopictus*. Its name comes from the Zika Forest of Uganda, where the virus was first isolated in 1947. Zika virus is related to the dengue, yellow fever, Japanese encephalitis, and West Nile viruses. Since the 1950s, it has been known to occur within a narrow equatorial belt from Africa to Asia. After being bitten, infected humans become the main carriers of Zika virus. The virus can spread farther and quicker due to human movement. For example, from 2007 to 2016, the virus spread eastward, across the Pacific Ocean to the Americas, leading to the 2015-2016 Zika virus epidemic.

The infection, known as Zika fever or Zika virus disease, often causes no symptoms or only mild symptoms, e.g., fever, headache, red eyes, skin rash, fatigue, muscle/joint pain, which is similar to a very mild form of dengue fever. While there is no specific treatment, acetaminophen and rest may help with the symptoms. As of 2016, the illness cannot be prevented by any medications or vaccines. Zika virus can spread through blood transfusion, sexual intercourse, and from a pregnant woman to her unborn baby, often resulting in microcephaly, severe brain damage and malformations, and other birth defects.

In January 2016, the United States Centers for Disease Control and Prevention (CDC) issued travel guidance on affected countries, including the use of enhanced precautions, and guidelines for pregnant women including considering postponing travel. Other governments or health agencies also issued similar travel warnings, while Colombia, the Dominican Republic, Puerto Rico, Ecuador, El Salvador, and Jamaica advised women to postpone getting pregnant until more is known about the risks.

Zika virus is a virus that has quickly made itself one of the world's biggest medical concerns. As the Zika virus epidemic progresses, the world remains unprepared to contain this threat as well as other similar mosquito-borne viral diseases, which can spontaneously become an epidemic in days. In a survey published by the Wall Street Journal, it was concluded that even the U.S. is not prepared to handle the demand for Zika virus testing in case of an actual epidemic. The current Zika virus testing method takes approximately 4-14 days; a time span that is completely unrealistic in the case of an epidemic occurring. Therefore, what is needed is a fast and convenient way to diagnose and/or estimate the probability that a person has been infected with Zika virus.

SUMMARY OF THE INVENTION

The disclosure addresses these problems and more by providing a fast and more efficient form for diagnosing the presence of Zika virus. In an embodiment, the disclosed computer implemented methods, processes, and systems utilize a computer program that uses different correlations and statistical tests to identify whether a human subject's eye manifests the symptoms of Zika virus.

Thus, in an embodiment the disclosure provides a computer implemented method of diagnosing whether a human subject is infected with Zika virus, which includes: a) determining a correlation between a fundus test image of an eye of the human subject for presence of gross macular pigment mottling with a known set of Zika virus infected fundus images and with a known set of healthy fundus images, wherein a high correlation between the fundus test image and the known set of Zika virus infected fundus images indicates that there is a high probability that the human subject is infected with Zika virus, wherein a low correlation between the fundus test image and the known set of Zika virus infected fundus images indicates that there is a low probability that the human subject is infected with Zika virus, wherein a high correlation between the fundus test image and the known set of healthy fundus images indicates that there is a low probability that the human subject is infected with Zika virus, and wherein a low correlation between the fundus test image and the known set of healthy fundus images indicates that there is a high probability that the human subject is infected with Zika virus.

In one aspect, the disclosure provides a computer implemented method, which further includes: b) determining whether a cup-to-disk ratio of the fundus test image of the eye of the human subject is within a predetermined threshold using edge detection methods, wherein when the cup-to-disk ratio exceeds the predetermined threshold, there is a high probability that the human subject is infected with Zika virus, and wherein when the cup-to-disk ratio falls below the predetermined threshold, there is a low probability that the human subject is infected with Zika virus.

In another aspect, the disclosure provides a computer implemented method, which further includes: c) determining whether a number of clusters representing regions of optic disc hypoplasia, are present within a predetermined range in the fundus test image of the eye of the human subject using k-means clustering, wherein when the number of clusters exceeds the predetermined range, there is a high probability that the human subject is infected with Zika virus, and wherein when the number of clusters falls below the predetermined range, there is a low probability that the human subject is infected with Zika virus.

In one aspect, the disclosure provides a computer implemented method, wherein a weighted score for steps a), b), and c) is used to indicate a probability that the human subject is infected with Zika virus.

In one aspect, the disclosure provides a computer implemented method, wherein the known set of healthy fundus images includes at least one of the human subject's prior healthy fundus image.

In another embodiment, the disclosure provides a non-transitory computer readable medium for storing a computer executable program that causes a processor to execute a process of estimating a probability that a human subject is infected with Zika virus, the process including: a) determining a correlation between a fundus test image of an eye of the human subject for presence of gross macular pigment mottling with a known set of Zika virus infected fundus images and with a known set of healthy fundus images, wherein a high correlation between the fundus test image and the known set of Zika virus infected fundus images indicates that there is a high probability that the human subject is infected with Zika virus, wherein a low correlation between the fundus test image and the known set of Zika virus infected fundus images indicates that there is a low probability that the human subject is infected with Zika virus, wherein a high correlation between the fundus test image and the known set of healthy fundus images indicates that there is a low probability that the human subject is infected with Zika virus, and wherein a low correlation between the fundus test image and the known set of healthy fundus images indicates that there is a high probability that the human subject is infected with Zika virus.

In one aspect, the disclosure provides a non-transitory computer readable medium, which further includes: b) determining whether a cup-to-disk ratio of the fundus test image of the eye of the human subject is within a predetermined threshold using edge detection methods, wherein when the cup-to-disk ratio exceeds the predetermined threshold, there is a high probability that the human subject is infected with Zika virus, and wherein when the cup-to-disk ratio falls below the predetermined threshold, there is a low probability that the human subject is infected with Zika virus.

In another aspect, the disclosure provides a non-transitory computer readable medium, which further includes: c) determining whether a number of clusters representing regions of optic disc hypoplasia, are present within a predetermined range in the fundus test image of the eye of the human subject using k-means clustering, wherein when the number of clusters exceeds the predetermined range, there is a high probability that the human subject is infected with Zika virus, and wherein when the number of clusters falls below the predetermined range, there is a low probability that the human subject is infected with Zika virus.

In another aspect, the disclosure provides a non-transitory computer readable medium, wherein a weighted score for steps a), b), and c) is used to indicate a probability that the human subject is infected with Zika virus.

In another aspect, the disclosure provides a non-transitory computer readable medium, wherein the known set of healthy fundus images includes at least one of the human subject's prior healthy fundus image.

In another embodiment, the disclosure provides a system, which includes: a smartphone having a fundus image analyzer app or a website having a fundus image analyzer; a first database having a known set of Zika virus infected fundus images; and a second database having a known set of healthy fundus images, wherein the smartphone having the fundus image analyzer app or the website having the fundus image analyzer determines: a) a correlation between a fundus test image of an eye of the human subject for presence of gross macular pigment mottling with a known set of Zika virus infected fundus images and with a known set of healthy fundus images, wherein a high correlation between the fundus test image and the known set of Zika virus infected fundus images indicates that there is a high probability that the human subject is infected with Zika virus, wherein a low correlation between the fundus test image and the known set of Zika virus infected fundus images indicates that there is a low probability that the human subject is infected with Zika virus, wherein a high correlation between the fundus test image and the known set of healthy fundus images indicates that there is a low probability that the human subject is infected with Zika virus, and wherein a low correlation between the fundus test image and the known set of healthy fundus images indicates that there is a high probability that the human subject is infected with Zika virus.

In one aspect, the disclosure provides a system, wherein the smartphone having the fundus image analyzer app or the website having the fundus image analyzer further determines: b) whether a cup-to-disk ratio of the fundus test image of the eye of the human subject is within a predetermined threshold using edge detection methods, wherein when the cup-to-disk ratio exceeds the predetermined threshold, there is a high probability that the human subject is infected with Zika virus, and wherein when the cup-to-disk ratio falls below the predetermined threshold, there is a low probability that the human subject is infected with Zika virus.

In another aspect, the disclosure provides a system, wherein the smartphone having the fundus image analyzer app or the website having the fundus image analyzer further determines: c) whether a number of clusters representing regions of optic disc hypoplasia, are present within a predetermined range in the fundus test image of the eye of the human subject using k-means clustering, wherein when the number of clusters exceeds the predetermined range, there is a high probability that the human subject is infected with Zika virus, and wherein when the number of clusters falls below the predetermined range, there is a low probability that the human subject is infected with Zika virus.

In another aspect, the disclosure provides a system, wherein a weighted score for steps a), b), and c) is used to indicate a probability that the human subject is infected with Zika virus.

In another aspect, the disclosure provides a system, wherein the known set of healthy fundus images includes at least one of the human subject's prior healthy fundus image.

DETAILED DESCRIPTION OF THE EMBODIMENTS

The disclosure provides a fast and efficient program for diagnosing the presence of Zika virus in an individual. The disclosed computer implemented methods, processes, and systems utilize a computer program that uses different statistical tests to identify whether a human subject's eye manifests the symptoms of Zika virus. For convenience, an online application and/or a smart phone app that analyzes the fundus images of the eye can be used to assess the probability that the person is infected with Zika virus.

Fundus photography involves capturing a photographic image of the back of the eye, i.e. the fundus. Specialized fundus cameras use a microscope and a flash attachment, which allows the camera to capture the fundus image. The main structures that can be visualized on a fundus photo are the central and peripheral retina, optic disc, and macula. fundus photography can be performed with colored filters, or with specialized dyes including fluorescein and indocyanine green.

Figure 1:
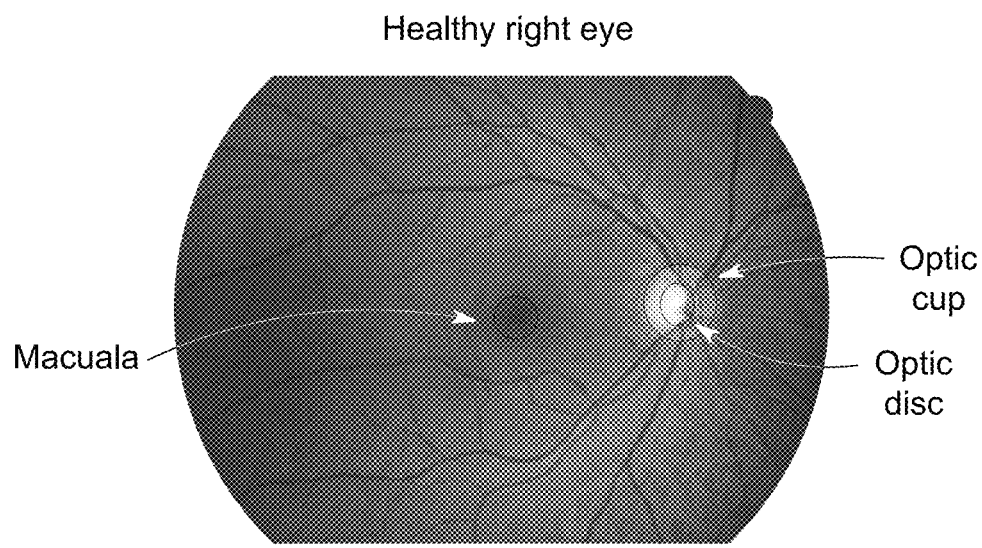
FIG. 1 illustrates a fundus photograph of a healthy eye as seen from the front so that left side in the image corresponds to the person's right side.

FIG. 1 illustrates a fundus photograph of a healthy eye as seen from the front so that left side in the image corresponds to the person's right side. The fundus image shows the retina—the inner third coat of the eye which is a light sensitive layer of tissue containing rod and cone cells; the macula—an oval-shaped pigmented area near the center of the retina containing predominantly cone cells in high density; and the optic disc and optic cup—the point of exit for ganglion cells leaving the eye and forming the beginning of the optic nerve, all of which show no sign of disease, disorder or pathology.

Once a person has been infected with Zika virus, they present three ocular symptoms: 1) gross macular pigment mottling, i.e., a discoloration of the macula; 2) an increased optic cup to optic disc ratio; and 3) optic nerve hypoplasia, i.e. the presence of a higher number of clusters representing white atrophic lesions. Each of these symptoms is visible in a fundus photograph, a photograph of the interior of the eye.

Figure 2:
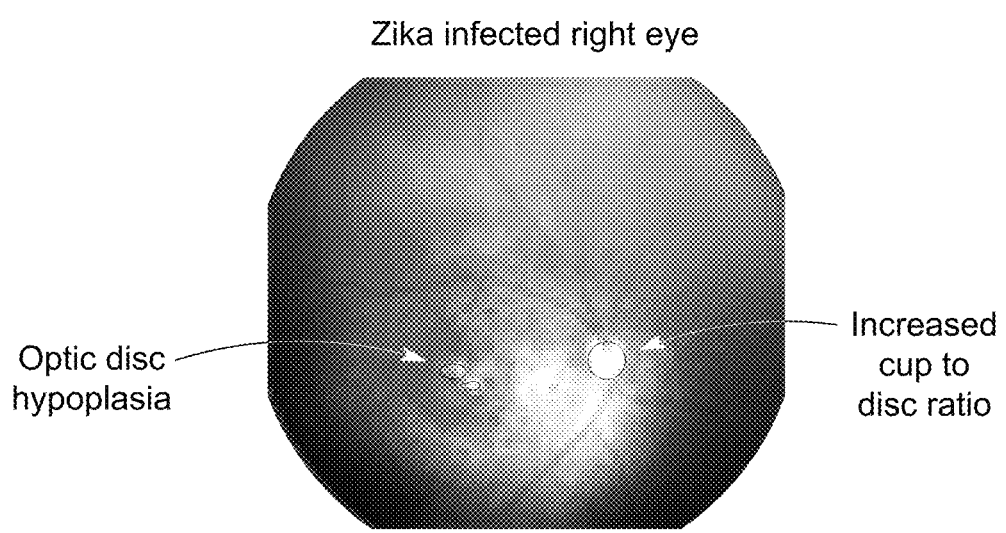
FIG. 2 illustrates a fundus photograph of the eye of a Zika virus infected individual.

FIG. 2 illustrates a fundus photograph of the eye of a Zika virus infected individual. This image demonstrates gross macular pigment mottling; an increased cup-to-disk ratio; and optic nerve hypoplasia, which are all characteristic of a Zika virus infected person's eye.

Figure 3:
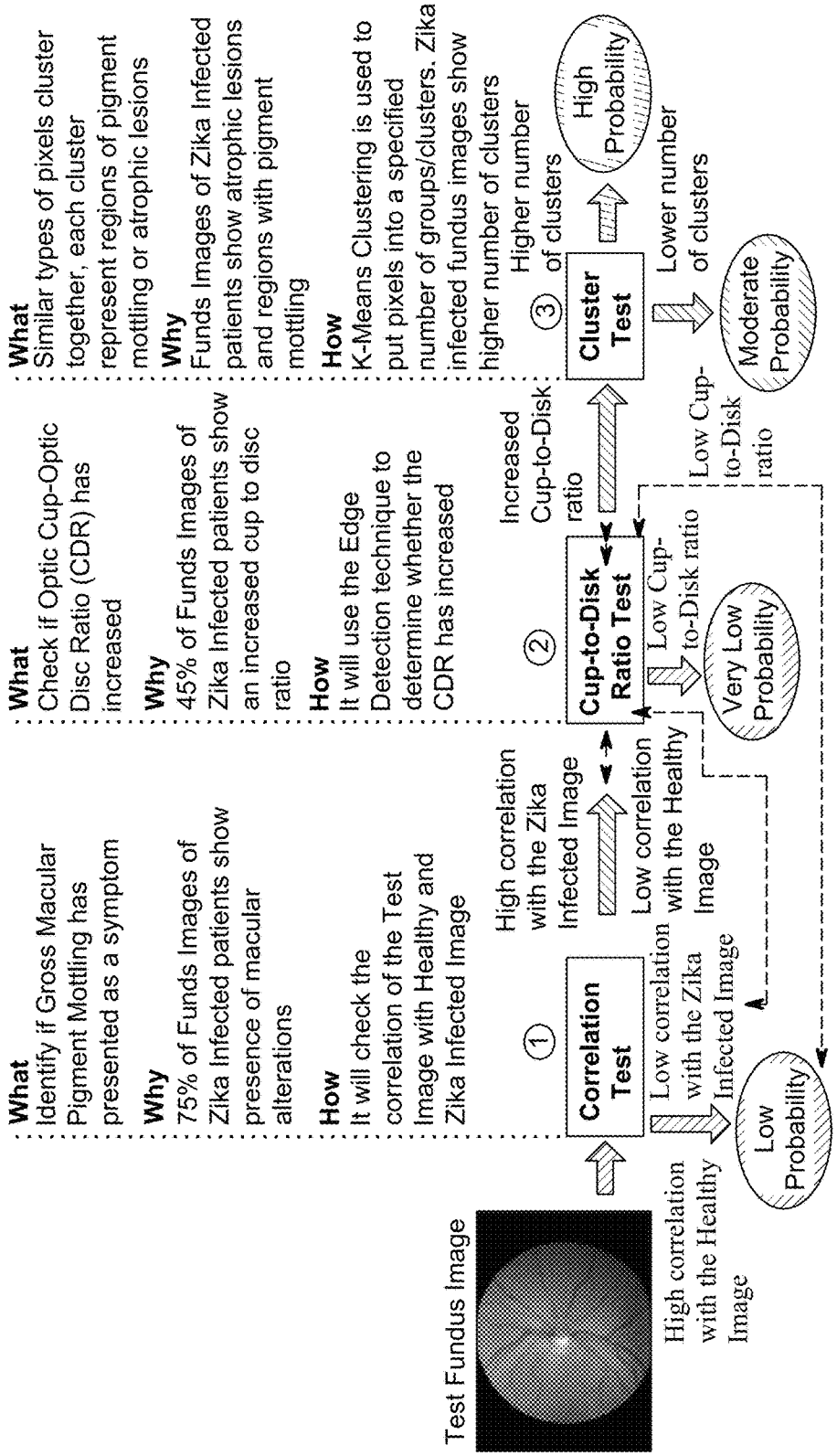
FIG. 3 illustrates an embodiment of three step process to estimate the probability that a human subject, i.e. a patient, is infected with Zika virus.

FIG. 3 illustrates a three-step process to estimate the probability that a human subject, i.e. a patient, is infected with Zika virus. Each step of the three-part analysis can produce a binary output on whether the person is likely to be infected with Zika virus or not. The final estimate may be based on the weighted scores of the outputs from these three tests. The program uses several tests including a correlation test, a cup-to-disk ratio test, and a cluster test to diagnose, determine or estimate the probability that a person is infected with Zika virus.

In step 1, a correlation test is used to analyze whether there is a correlation between a fundus test image of an eye of a human subject for the presence of gross macular pigment mottling with a known set of Zika virus infected fundus images and with a known set of healthy fundus images or the subjects' prior healthy fundus image. 75% of fundus images of Zika infected patients show the presence of macular alterations. A high correlation between the fundus test image and the known set of Zika virus infected fundus images indicates a high probability that the human subject is infected with Zika virus; a low correlation between the fundus test image and the known set of Zika virus infected fundus images indicates a low probability that the human subject is infected with Zika virus; a high correlation between the fundus test image and the known set of healthy fundus images indicates a low probability that the human subject is infected with Zika virus, and a low correlation between the fundus test image and the known set of healthy fundus images indicates a high probability that the human subject is infected with Zika virus.

While absolute numbers for a high probability and/or a low probability are not feasible, generally a high probability means more than a 50% chance, or more than a 60% chance, or more than a 70% chance, or more than an 80% chance, or more than a 90% chance or nearly a 100% chance of an event occurring, i.e. the probability that a human subject is infected with Zika virus. Conversely, generally a low probability means less than a 50% chance, or less than a 40% chance, or less than a 30% chance, or less than a 20% chance, or less than a 10% chance, or nearly a 0% chance of an event occurring, i.e. the probability that a human subject is infected with Zika virus.

As stated above, the first step of the program analyzes for a correlation between the fundus test image and two sets of images, i.e. Zika virus infected fundus images, and the set of healthy fundus images or the subject's prior healthy fundus image. Specifically, the program compares the RGB values of every pixel in the fundus test image to the RGB values of the corresponding pixels for both Zika virus infected fundus images and the set of healthy fundus images. Numerically, it identifies the correlation between three data sets with approximately 12,000,000 values for each. This section of the code digitally does the equivalent of a human telling the difference between three images, however the program will take a few seconds and will be accurate and highly precise. The program can calculate and print the correlation, the correlation being between the fundus test image and the Zika infected fundus image; and the correlation between the fundus test image and the set of healthy fundus images. A high correlation with the set of Zika infected fundus images and a low correlation with the set of healthy fundus images indicate that the person is likely infected with Zika virus, and vice versa.

If there is a high probability that the human subject is infected with Zika virus, then the process proceeds to step 2.

In step 2, a cup-to-disk ratio test is used to determine whether the fundus test image of the eye of the human subject is within a predetermined threshold using edge detection methods, wherein if the cup-to-disk ratio exceeds the predetermined threshold, this indicates a diagnosis that the human subject is infected with Zika virus, and wherein if the cup-to-disk ratio falls below the predetermined threshold, this indicates a diagnosis that the human subject is not infected with Zika virus.

The rationale behind this test is that with an individual with a Zika virus infected eye, there is a high probability that it will have a high cup-to-disc ratio. For example, 45% of fundus images of Zika virus infected patients show an increased cup-to-disk ratio. The purpose of this section is to find that ratio and determine whether that value is above average. The program does this through edge detection methods.

Edge detection methods are an image processing technique whose purpose is to find the boundaries of an object within an image. In this scenario, those boundaries are the cup and disc of the eye. The program analyzes a group of pixels localized near the center of the retina, and using the edge detection methods it will find the edge of the optic cup as well as the edge of the optic disc. After collecting these two data points, the program is then able to calculate the cup-to-disc ratio. By finding the edges of both the cup and disc, the program then computes the size ratio between the two objects, which it then compares to the normal ratio. Through this comparison it determines whether the cup-to-disk ratio is within an acceptable range. In Zika infected fundus images, the cup-to-disk ratio is much higher than the normal cup-to-disk ratio, which indicates the presence of Zika virus.

In step 3, a cluster test is used to determine whether a number of data clusters present in a dataset of RGB values of the fundus test image of the eye of the human subject is within a predetermined range using k-means clustering to determine if optic disc hypoplasia is present, wherein if the number of data clusters exceeds the predetermined range and optic disc hypoplasia is present, this indicates a diagnosis that the human subject is infected with Zika virus, and wherein if the number of data clusters falls below the predetermined range and optic disc hypoplasia is not present, this indicates a diagnosis that the human subject is not infected with Zika virus.

The cluster test is used to determine the presence of clusters representing regions of atrophic lesions or optic disc hypoplasia in the fundus test image of an eye of the human subject. Similar types of pixels cluster together, each cluster represent regions of atrophic lesions or optic disc hypoplasia. When infected with the Zika virus, there is a strong probability white patches will appear within the fundus which will be invisible to the naked eye. This part of the program uses a data analysis technique known as k-means clustering to find these clusters. The technique of k-means clustering is applied to a data set containing the RGB values of the image. By finding the clusters of RGB values the program can locate white spots in the image. In addition, the program also determines if the number of clusters is within range, under the rationale that a Zika virus infected fundus image will have a higher number of clusters due to the white atrophic lesions.

Through these three "checks" the program reduces the chance of a false positive, while also testing the variable image within seconds. A high number of clusters imply the presence of atrophic lesions or optic disc hypoplasia in the eye, indicating the presence of Zika virus infection. The weighted score of these three tests can be used to estimate the probability that a person is infected with Zika virus or not.

Example

A dataset of 177 fundus images was examined: 7 images were from patients having Zika virus; 100 images were from patients without any eye diseases or disorders; 50 images were from patients having glaucoma; and 20 images were from patients having other degenerative eye diseases. After each imaged had been analyzed by the above described three step program, the program output successfully identified the 7 images from patients having Zika virus and had an overall 99.5% success rate with an average run time of 47 seconds.

The significance of this process can be found in the situation of a Zika Epidemic. Previously, tens of thousands of people sent their blood samples to the CDC or any equivalent testing lab and waited 4-14 days to determine their Zika virus status. However, now the individual or their healthcare provider can easily make the diagnosis using an app on their smart phone and within a minute of their time, can know their status. Public health officials can use this service to scan large group of Airline and Cruise passengers to identify people who might be infected with Zika virus.

As stated above, an online website application and/or a smart phone app that analyzes the fundus images of the eye can be used to assess the probability that the person is infected with Zika virus. A fundus image of a retina can be made using a smart phone, which can be submitted for analysis using an app to an analysis website. The web server analyzes the fundus image using the combination of analysis described above. Finally, a probability estimate is outputted to the user through their smart phone or website portal, which indicates the likelihood that the person is infected with Zika virus.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are accordingly to be regarded in an illustrative rather than in a restrictive sense.

What is claimed is:

1. A computer implemented method of diagnosing whether a human subject is infected with Zika virus, comprising:
a) determining a correlation between a fundus test image of an eye of the human subject for presence of gross macular pigment mottling with a known set of Zika virus infected fundus images and with a known set of healthy fundus images,
wherein a high correlation between the fundus test image and the known set of Zika virus infected fundus images indicates that there is a high probability that the human subject is infected with Zika virus,
wherein a low correlation between the fundus test image and the known set of Zika virus infected fundus images indicates that there is a low probability that the human subject is infected with Zika virus,
wherein a high correlation between the fundus test image and the known set of healthy fundus images indicates that there is a low probability that the human subject is infected with Zika virus, and
wherein a low correlation between the fundus test image and the known set of healthy fundus images indicates that there is a high probability that the human subject is infected with Zika virus.

2. The computer implemented method of claim 1, further comprising:
b) determining whether a cup-to-disk ratio of the fundus test image of the eye of the human subject is within a predetermined threshold using edge detection methods,
wherein when the cup-to-disk ratio exceeds the predetermined threshold, there is a high probability that the human subject is infected with Zika virus, and
wherein when the cup-to-disk ratio falls below the predetermined threshold, there is a low probability that the human subject is infected with Zika virus.

3. The computer implemented method of claim 2, further comprising:
c) determining whether a number of clusters representing regions of optic disc hypoplasia, are present within a predetermined range in the fundus test image of the eye of the human subject using k-means clustering,
wherein when the number of clusters exceeds the predetermined range, there is a high probability that the human subject is infected with Zika virus, and
wherein when the number of clusters falls below the predetermined range, there is a low probability that the human subject is infected with Zika virus.

4. The method of claim 1, further comprising:
b) determining whether a cup-to-disk ratio of the fundus test image of the eye of the human subject is within a predetermined threshold using edge detection methods,
wherein when the cup-to-disk ratio exceeds the predetermined threshold, there is a high probability that the human subject is infected with Zika virus, and
wherein when the cup-to-disk ratio falls below the predetermined threshold, there is a low probability that the human subject is infected with Zika virus; and
c) determining whether a number of clusters representing regions of optic disc hypoplasia, are present within a predetermined range in the fundus test image of the eye of the human subject using k-means clustering,
wherein when the number of clusters exceeds the predetermined range, there is a high probability that the human subject is infected with Zika virus, and
wherein when the number of clusters falls below the predetermined range, there is a low probability that the human subject is infected with Zika virus, and
wherein a weighted score for steps a), b), and c) is used to indicate a probability that the human subject is infected with Zika virus.

5. The method of claim 1, wherein the known set of healthy fundus images includes at least one of the human subject's prior healthy fundus image.

6. A non-transitory computer readable medium for storing a computer executable program that causes a processor to execute a process of estimating a probability that a human subject is infected with Zika virus, the process comprising:

a) determining a correlation between a fundus test image of an eye of the human subject for presence of gross macular pigment mottling with a known set of Zika virus infected fundus images and with a known set of healthy fundus images, wherein a high correlation between the fundus test image and the known set of Zika virus infected fundus images indicates that there is a high probability that the human subject is infected with Zika virus, wherein a low correlation between the fundus test image and the known set of Zika virus infected fundus images indicates that there is a low probability that the human subject is infected with Zika virus, wherein a high correlation between the fundus test image and the known set of healthy fundus images indicates that there is a low probability that the human subject is infected with Zika virus, and wherein a low correlation between the fundus test image and the known set of healthy fundus images indicates that there is a high probability that the human subject is infected with Zika virus.

7. The non-transitory computer readable medium of claim 6, further comprising:

b) determining whether a cup-to-disk ratio of the fundus test image of the eye of the human subject is within a predetermined threshold using edge detection methods, wherein when the cup-to-disk ratio exceeds the predetermined threshold, there is a high probability that the human subject is infected with Zika virus, and wherein when the cup-to-disk ratio falls below the predetermined threshold, there is a low probability that the human subject is infected with Zika virus.

8. The non-transitory computer readable medium of claim 7, further comprising:

c) determining whether a number of clusters representing regions of optic disc hypoplasia, are present within a predetermined range in the fundus test image of the eye of the human subject using k-means clustering, wherein when the number of clusters exceeds the predetermined range, there is a high probability that the human subject is infected with Zika virus, and wherein when the number of clusters falls below the predetermined range, there is a low probability that the human subject is infected with Zika virus.

9. The non-transitory computer readable medium of claim 6, further comprising:

b) determining whether a cup-to-disk ratio of the fundus test image of the eye of the human subject is within a predetermined threshold using edge detection methods, wherein when the cup-to-disk ratio exceeds the predetermined threshold, there is a high probability that the human subject is infected with Zika virus, and wherein when the cup-to-disk ratio falls below the predetermined threshold, there is a low probability that the human subject is infected with Zika virus;

c) determining whether a number of clusters representing regions of optic disc hypoplasia, are present within a predetermined range in the fundus test image of the eye of the human subject using k-means clustering, wherein when the number of clusters exceeds the predetermined range, there is a high probability that the human subject is infected with Zika virus, and wherein when the number of clusters falls below the predetermined range, there is a low probability that the human subject is infected with Zika virus, and wherein a weighted score for steps a), b), and c) is used to indicate a probability that the human subject is infected with Zika virus.

10. The non-transitory computer readable medium of claim 6, wherein the known set of healthy fundus images includes at least one of the human subject's prior healthy fundus image.

11. A system, comprising:

a smartphone having a fundus image analyzer app or a website having a fundus image analyzer, a first database having a known set of Zika virus infected fundus images; and a second database having a known set of healthy fundus images, wherein the smartphone having the fundus image analyzer app or the website having the fundus image analyzer determines:

a) a correlation between a fundus test image of an eye of the human subject for presence of gross macular pigment mottling with a known set of Zika virus infected fundus images and with a known set of healthy fundus images, wherein a high correlation between the fundus test image and the known set of Zika virus infected fundus images indicates that there is a high probability that the human subject is infected with Zika virus, wherein a low correlation between the fundus test image and the known set of Zika virus infected fundus images indicates that there is a low probability that the human subject is infected with Zika virus, wherein a high correlation between the fundus test image and the known set of healthy fundus images indicates that there is a low probability that the human subject is infected with Zika virus, and wherein a low correlation between the fundus test image and the known set of healthy fundus images indicates that there is a high probability that the human subject is infected with Zika virus.

12. The system of claim 11, wherein the smartphone having the fundus image analyzer app or the website having the fundus image analyzer further determines:

b) whether a cup-to-disk ratio of the fundus test image of the eye of the human subject is within a predetermined threshold using edge detection methods, wherein when the cup-to-disk ratio exceeds the predetermined threshold, there is a high probability that the human subject is infected with Zika virus, and wherein when the cup-to-disk ratio falls below the predetermined threshold, there is a low probability that the human subject is infected with Zika virus.

13. The system of claim 11, wherein the smartphone having the fundus image analyzer app or the website having the fundus image analyzer further determines:

c) whether a number of clusters representing regions of optic disc hypoplasia, are present within a predetermined range in the fundus test image of the eye of the human subject using k-means clustering, wherein when the number of clusters exceeds the predetermined range, there is a high probability that the human subject is infected with Zika virus, and wherein when the number of clusters falls below the predetermined range, there is a low probability that the human subject is infected with Zika virus.

14. The system of claim 11, wherein the smartphone having the fundus image analyzer app or the website having the fundus image analyzer further determines:

b) whether a cup-to-disk ratio of the fundus test image of the eye of the human subject is within a predetermined threshold using edge detection methods, wherein when the cup-to-disk ratio exceeds the predetermined threshold, there is a high probability that the human subject is infected with Zika virus, and wherein when the cup-to-disk ratio falls below the predetermined threshold, there is a low probability that the human subject is infected with Zika virus; and c) whether a number of clusters representing regions of optic disc hypoplasia, are present within a predetermined range in the fundus test image of the eye of the human subject using k-means clustering, wherein when the number of clusters exceeds the predetermined range, there is a high probability that the human subject is infected with Zika virus, and wherein when the number of clusters falls below the predetermined range, there is a low probability that the human subject is infected with Zika virus, and wherein a weighted score for steps a), b), and c) is used to indicate a probability that the human subject is infected with Zika virus.

15. The system of claim 11, wherein the known set of healthy fundus images includes at least one of the human subject's prior healthy fundus image.

* * * * *